United States Patent
Kelly et al.

(10) Patent No.: US 10,402,926 B2
(45) Date of Patent: Sep. 3, 2019

(54) MULTIDEVICE COLLABORATION

(75) Inventors: Lisa Kelly, Overland Park, KS (US);
Amanda Buckley, Olathe, KS (US);
Stephanie L. Rogers, Kansas City, MO
(US); Robert Farr, Jr., Liberty, MO
(US)

(73) Assignee: CERNER INNOVATION, INC.,
Kansas City, KS (US)

( * ) Notice: Subject to any disclaimer, the term of this
patent is extended or adjusted under 35
U.S.C. 154(b) by 1177 days.

(21) Appl. No.: 13/341,480

(22) Filed: Dec. 30, 2011

(65) Prior Publication Data

US 2013/0173291 A1 Jul. 4, 2013

(51) Int. Cl.
*G06Q 10/10* (2012.01)
*G06Q 50/22* (2018.01)
*G06Q 50/24* (2012.01)

(52) U.S. Cl.
CPC ........... *G06Q 50/24* (2013.01); *G06Q 10/103*
(2013.01); *G06Q 50/22* (2013.01)

(58) Field of Classification Search
CPC ............................ A06F 19/3406; G06Q 50/24
USPC ........................................................ 715/835
See application file for complete search history.

(56) References Cited

U.S. PATENT DOCUMENTS

| | | | |
|---|---|---|---|
| 5,760,704 A * | 6/1998 | Barton et al. ............. 340/286.07 |
| 7,454,462 B2 * | 11/2008 | Belfiore et al. ............... 709/203 |
| 7,612,679 B1 * | 11/2009 | Fackler et al. ............... 340/573.1 |
| 7,895,527 B2 * | 2/2011 | Zaleski et al. .................. 715/804 |
| 8,700,423 B2 * | 4/2014 | Eaton, Jr. .............. G06Q 10/087 701/400 |
| 8,793,618 B2 * | 7/2014 | Martin ................ G06F 19/3406 715/774 |
| 8,956,292 B2 * | 2/2015 | Wekell ............... A61B 5/02055 600/301 |
| 8,972,272 B1 * | 3/2015 | Dvorak et al. ..................... 705/3 |
| 9,492,341 B2 * | 11/2016 | Huster ................. A61B 5/1115 |
| 2002/0035484 A1 * | 3/2002 | McCormick ....................... 705/2 |
| 2008/0010089 A1 * | 1/2008 | DiMaggio et al. ............... 705/2 |
| 2008/0052124 A1 * | 2/2008 | Goodman et al. ................ 705/3 |
| 2009/0055735 A1 * | 2/2009 | Zaleski et al. ................ 715/700 |
| 2010/0293003 A1 * | 11/2010 | Abbo ............................... 705/2 |
| 2012/0179490 A1 * | 7/2012 | Fuhrmann et al. ............... 705/3 |

OTHER PUBLICATIONS

Google patents search, Jul. 24, 2017.*
Gogple patents search, Apr. 19, 2019.*

* cited by examiner

*Primary Examiner* — Dilek B Cobanoglu
(74) *Attorney, Agent, or Firm* — Shook, Hardy & Bacon L.L.P.

(57) ABSTRACT

Systems, methods, and computer-readable media for multidevice collaboration are provided. In embodiments, indications are provided on a device that a wrong chart is open for a location. A clinician is prompted to synchronize a chart with a dashboard associated with the location. Control of the dashboard is transferred to the clinician utilizing the device.

20 Claims, 20 Drawing Sheets

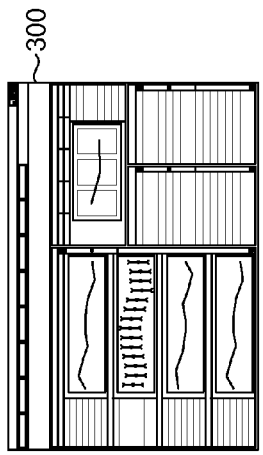
FIG. 3A
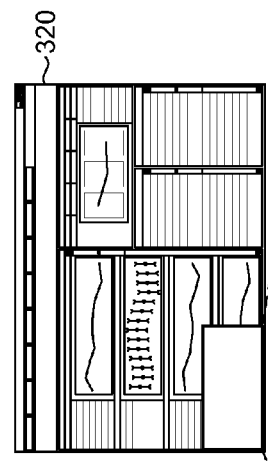
FIG. 3C
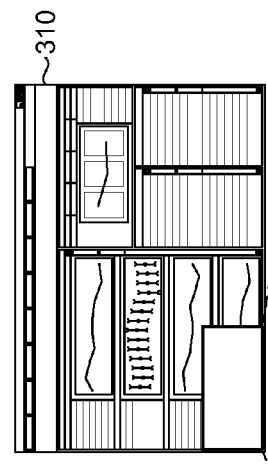
FIG. 3B
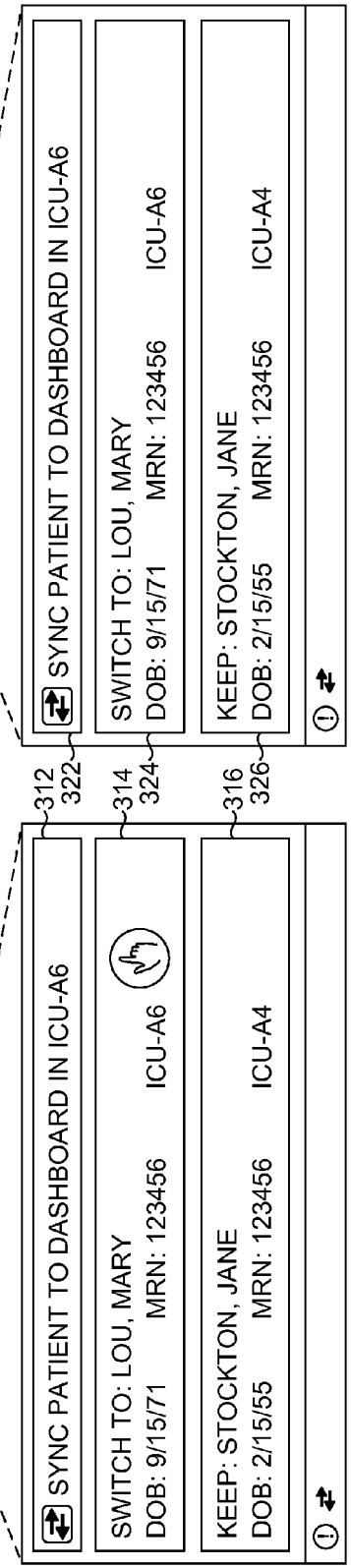

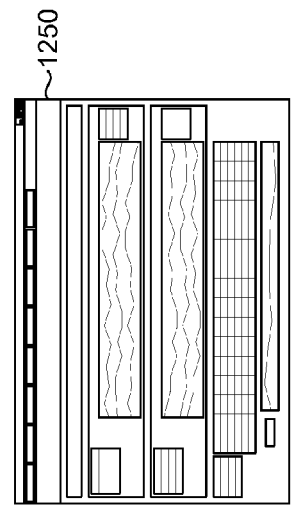
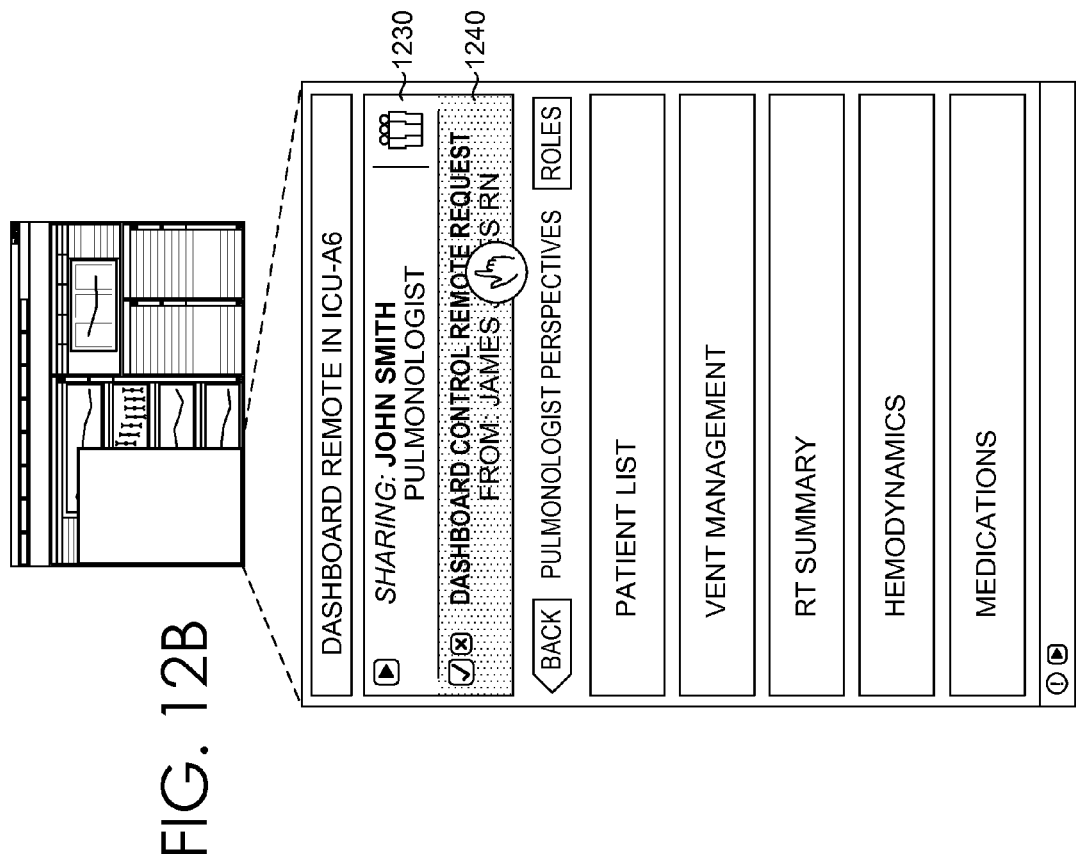
FIG. 12C
FIG. 12B

MULTIDEVICE COLLABORATION

BACKGROUND

In order to provide effective and efficient management of healthcare environments, healthcare institutions are using a variety of healthcare management systems. Such healthcare management systems may monitor the locations of patients and providers. Recent developments in healthcare have caused an increase in the use of electronic medical records (EMR's) and electronic storage of a variety of clinical information.

Patient medical information, such as that contained in the EMR, allows health care providers to provide continuity of care to patients. Thus, it is critical for clinicians providing care to patients to review and collaborate with other clinicians for each patient's medical record. The growth in access to and utilization of electronic medical records by healthcare providers and facilities has significantly reduced the time and organization efforts required by paper medical records. Unfortunately, this growth has introduced new problems. Medical records associated with the incorrect patient are often mistakenly viewed without knowledge by the clinician. For example, the clinician may enter a particular location, such as a patient room, with a workstation on wheels (WOW), a mobile computing device, or a handheld computer device and forget to open the EMR for the patient associated with that location. In other cases, it is difficult for clinicians to collaborate with respect to the patient chart or dashboard that may be available on a display device within that particular location because peripheral devices, such as a mouse or keyboard, utilized to control the dashboard are often missing. In still other cases, a particular view of the dashboard associated with a particular clinician or particular role may be necessary to share among various parties for collaboration or learning purposes, but may be unavailable due to security or regulatory concerns.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to facilitating multidevice collaboration in a clinical computing environment. When a device enters a location, an indication is provided on the device that a wrong chart is open for that location. A clinician is prompted to synchronize a chart with a dashboard associated with the location. Control of the dashboard is transferred to the clinician utilizing the device. Requests from other clinicians may be received to share control of the dashboard utilizing other devices. Personalized views of the dashboard may be displayed utilizing perspectives and gadgets associated with various roles.

BRIEF DESCRIPTION OF THE DRAWING

The present invention is described in detail below with reference to the attached drawing figures, wherein:

FIGS. 3A-3D are illustrative graphical user interface displays of synchronizing a chart with a dashboard associated with a location, in accordance with embodiments of the present invention;

FIGS. 12A-12C are illustrative graphical user interface displays of sharing control of personalized views, in accordance with an embodiment of the present invention;

DETAILED DESCRIPTION

Figure 1:
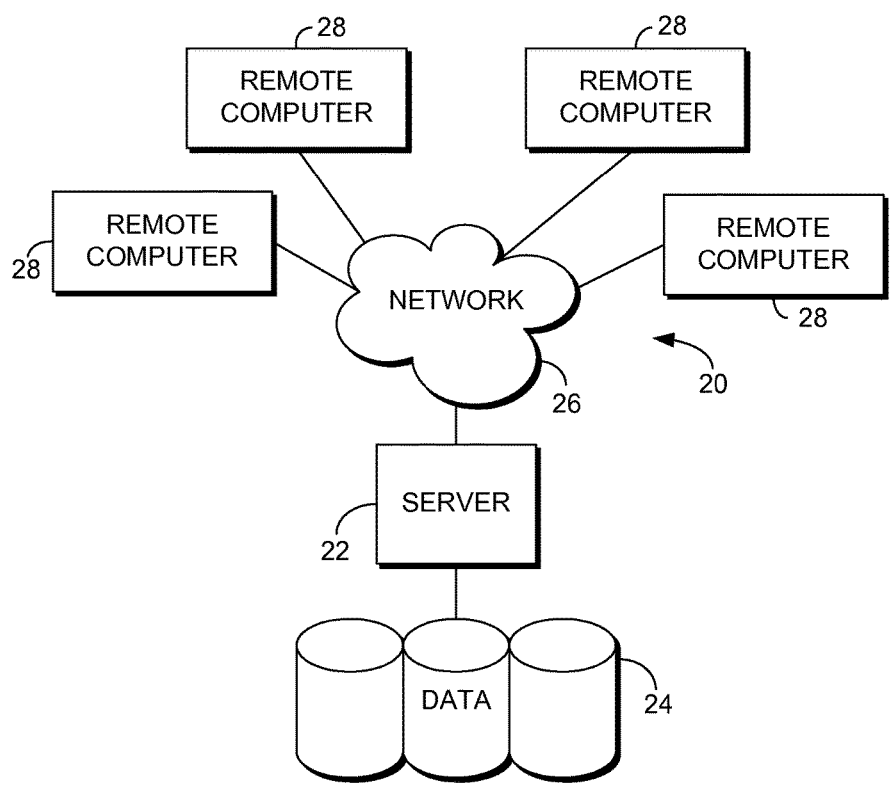
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention can positively impact health organizations' key imperatives in a variety of ways. Embodiments of the present invention provide indications on a clinician's device when a wrong chart is open for a location and prompt the clinician to synchronize a chart with a dashboard associated with the location. Embodiments of the present invention allow clinicians to request and share control of the dashboard utilizing their own device. Embodiments of the present invention allow clinicians to share views, perspectives, and gadgets associated with their role. Embodiments of the present invention allow clinicians to display role views associated with a role of another clinician.

Accordingly, in one aspect, an embodiment of the present invention is directed to a method that facilitates multidevice collaboration. The method includes providing an indication on a first device that a wrong chart is open for a location. The method also includes prompting a first clinician to synchronize a chart with a dashboard associated with the location. The method further includes transferring control of the dashboard to the first clinician utilizing the first device.

In another aspect, an embodiment of the present invention is directed to system environment for providing facilitating multidevice collaboration. The system includes a processor coupled to a computer storage medium. A plurality of computer software components executable by the processor are stored on the computer storage medium. A notification component notifies a first device that a wrong chart is open for a location. A synchronization component prompts a first clinician to synchronize a chart with a dashboard associated with the location. A transfer component transfers control of the dashboard to the first clinician utilizing the first device. A modification component allows the first clinician to modify views on the dashboard utilizing the first device. A personalized view component displays a personalized view associated with a role of the first clinician.

In another aspect, an embodiment of the present invention is directed to a graphical user interface (GUI) to facilitate multidevice collaboration. Computer-executable instructions are embodied on computer storage media and, when executed, produce a GUI. The GUI comprises a first display area that displays a notification that a wrong chart is open for a location. A second display area displays a prompt for a clinician to synchronize a chart with a dashboard associated with the location. A third display area displays a clinician view of the dashboard. A fourth display area displays a request from a second clinician to share control of the dashboard utilizing a second device. A fifth display area displays a personalized view associated with a role of the first clinician.

Referring now to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and non-volatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnections are well known. Accordingly, additional details concerning the internal construction of the server 22 and the remote computers 28 are not further disclosed herein.

Clinical integration of a healthcare management system with patients' electronic medical records offer the most efficient healthcare management system by tracking healthcare resources such that the system is aware of the location of healthcare resources and devices and may use the location awareness in combination with clinical information stored in an EMR.

Healthcare resources such as clinicians, patients, equipment, clinical devices, and the like may be tracked via a plurality of sensors in the healthcare environment. The sensors in the healthcare environment may utilize ultrasound technology, infrared technology, radio-frequency identification technology, and the like. Using said technology, the sensors send out signals to clinician identifiers, patient identifiers, item identifiers, clinical device identifiers, or the like. An exemplary sensor system is the Cricket Indoor Location System sponsored by the MIT Project Oxygen partnership.

The signals are received by the identifiers and the identifiers respond to the signals. A response from an identifier is received by the sensors and the sensors are able to recognize and determine the location of the responding identifier and, thus, are aware of the resources within the healthcare environment. The respective identifiers associated with the resources may be located, e.g., on the person, on the item, or on the device. Exemplary identifiers include badges, wristbands, tags, and the like. The locations of clinicians, patients, equipment, or the like, associated with a responding identifier, may be presented or displayed on a display of a computing device, such as remote computer 108 of FIG. 1.

The presence of the clinicians, patients, clinical devices, or the like, is useful when determining whether a clinician has the proper chart displayed on a device based on the detecting whether the clinician is near the patient associated with the chart displayed on the clinician's device. Additionally, the presence information may be used in combination with clinical information from an EMR or with an alert presented based on clinical information, location information, clinical device information, or a combination thereof.

Figure 2:
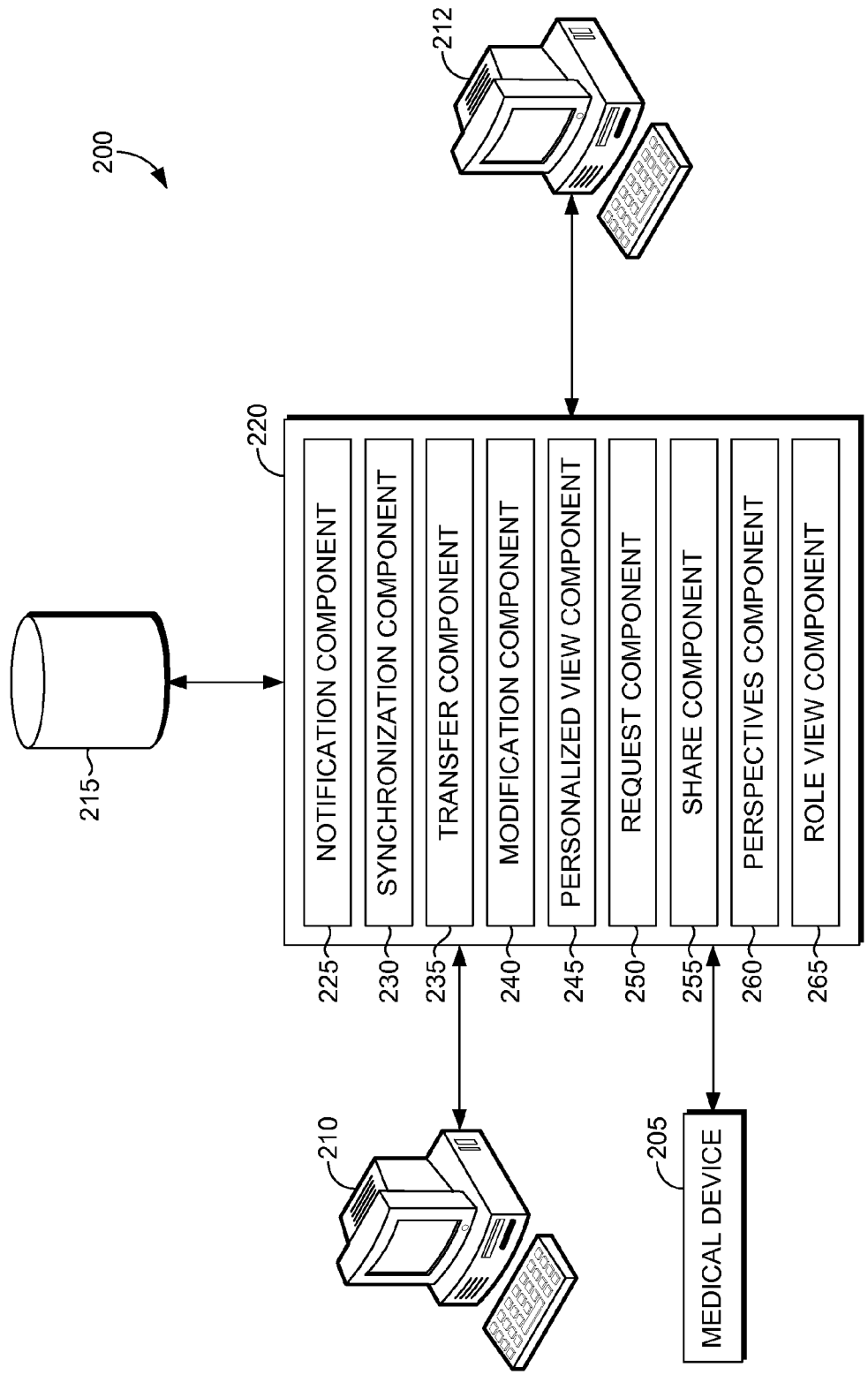
FIG. 2 is a block diagram of an exemplary system for facilitating multidevice collaboration, in accordance with an embodiment of the present invention.

With reference to FIG. 2, a block diagram is illustrated that shows an exemplary computing system architecture for automatically opening and closing patient information. It will be appreciated that the computing system architecture shown in FIG. 2 is merely an example of one suitable computing system and is not intended as having any dependency or requirement related to any single module/component or combination of modules/components.

The computing system includes one or more medical devices 205, a first device 210, a second device 212, datastore 215, and multidevice collaboration module 220. Data elements are received from medical devices 205. A medical device 205 may be any device, stationary or otherwise, that may be used to treat, diagnose, monitor, or measure aspects of a patient in a hospital, doctor's office, etc. For exemplary purposes only and not limitation, medical devices include cardiac monitors, cardiac output monitors, ICP monitors, ventilators, pumps (e.g., infusion pumps, balloon pumps), and the like. As such, these medical devices generate various data (e.g., heart-rate changes) that is communicated to datastore 215.

Datastore 215 contains a variety of information data for the patient in a patient's electronic medical record (EMR). As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare. Devices 210,212 may be a workstation on wheels (WOW), a handheld computing device, a mobile device, or any other hardware device for displaying output and capable of displaying graphical user interfaces.

Multidevice collaboration module 220 receives and displays data from datastore 215 and/or one or more medical devices 205 for a patient. Multidevice collaboration module 220 may reside on one or more computing devices, such as, for example, the control server 12 described above with reference to FIG. 1. By way of example, the control server 12 includes a computer processor and may be a server, personal computer, desktop computer, laptop computer, handheld device, mobile device, consumer electronic device, or the like.

Multidevice collaboration module 220 comprises notification component 225, synchronization component 230, transfer component 235, modification component 240, and personalized view component 245. In various embodiments, multidevice collaboration module 220 includes request component 250, share component 255, perspectives component 260, and role view component 265.

It will be appreciated that while multidevice collaboration module 220 is depicted as being connected to a single medical device 205 and datastore 215 and two devices 210, 212, multidevice collaboration module 220 may receive data from multiple medical devices and/or datastores including for multiple patients at multiple locations and may be in communication with multiple clinicians utilizing multiple devices.

Notification component 225 notifies a first device 210 that a wrong chart is open for a location. A first clinician possessing the first device 210 may have entered the location from a previous location and still have the chart associated with the previous location open on the first device 210. Thus, by utilizing presence awareness discussed above, the notification component determines that, based on the location, the clinician does not have the proper chart open. In another embodiment, the notification component determines that, based on the patient the clinician is near, the clinician does not have the proper chart open. This is particularly useful, for example, when a specific location has more than one patient associated with that location. Accordingly, the notification component 225 sends a notification to the first device 210 alerting the clinician that the wrong chart is open for the present location or patient.

Synchronization component 230 prompts a first clinician to synchronize a chart with a dashboard associated with the location. In another embodiment, synchronization component 230 prompts the first clinician to synchronize a chart with a dashboard associated with the patient the first clinician is near. Again, by utilizing presence awareness, the chart on the first device will be synchronized with the dashboard in the location the first clinician has entered. In another embodiment, the chart on the first device is synchronized with the dashboard associated with the patient that is near the first clinician. This ensures that the clinician does not mistakenly view the wrong chart when assessing or treating the patient in that location or near that clinician. As can be appreciated, automatically synchronizing or prompting a clinician to synchronize the chart with a dashboard based on presence also prevents charting errors that may otherwise occur if a clinician begins charting without realizing that the wrong chart is open.

Transfer component 235 transfers control of the dashboard to the first clinician utilizing the first device. Since it is often difficult to access or find an input device (e.g., a mouse or keyboard) attached to the dashboard in a room, the transfer component transfers control of the dashboard to the first clinician utilizing the first device as soon as the first device is synchronized. This gives the clinician control of the dashboard as may be necessary when collaborating with other clinicians or to assist in educating families regarding the condition or treatment of a loved one.

Modification component 240 allows the first clinician to modify views on the dashboard utilizing the first device. As noted above, the first clinician may be collaborating with other clinicians and may need to modify the view of the dashboard accordingly. Similarly, when educating families regarding the condition or treatment of a loved one, a clinician may need to be able to modify the view of the dashboard such that a high level view can be provided that is more easily understood or does not raise any regulatory or security concerns. The modification component allows the clinician to control the view that is displayed on the dashboard for others by utilizing the first device. In one embodiment, the view that is displayed on the dashboard is independent of the view that is displayed on the first device. For example, while educating the family of a patient regarding the condition of that patient, a clinician may desire to display only certain elements of the display on the first device. Accordingly, the clinician modifies the view on the dashboard to display only the information the clinician wishes to share, while retaining the full display on the first device.

Personalized view component 245 displays a personalized view associated with a role of the first clinician. This allows the display on the dashboard to reflect the view associated with the role of the first clinician. For example, a pulmonologist may typically see a different display of the dashboard than the attending physician. Similarly, a clinician associated with a pharmacy may have a different display of the dashboard than the pulmonologist. As can be appreciated the personalized view component 245 allows the first clinician to display the personalized view associated with the role of the first clinician on the dashboard. This allows other clinicians to more effectively collaborate with the first clinician, particularly when the first clinician is able to display a view that may not be readily available for other clinicians.

In one embodiment, request component 250 receives requests from a second clinician requesting control of the dashboard utilizing a second device. Suppose a second clinician enters the location where a first clinician has already received control of the dashboard. As the second clinician is detected as near the patient associated with that location or dashboard, the second clinician determines that she needs control of the dashboard to communicate or collaborate with the patient or first clinician. The second clinician can initiate a request to control the dashboard utilizing the second device.

After request component 250 receives the request from the second clinician to control the dashboard utilizing the second device, in one embodiment, share component 255 transfers control of the dashboard to the second clinician utilizing the second device. In one embodiment, control of the dashboard is transferred upon receiving the request. In another embodiment, first clinician must acknowledge the request before share component 255 transfers control of the dashboard to the second clinician. In another embodiment, share component 255 transfers control after a predetermined amount of time after request component 250 receives the request, allowing the first clinician time to complete any necessary or desired actions prior to control being transferred to the second clinician.

In one embodiment, perspectives component 260 enables perspectives and gadgets associated with the role. Referring back to the personalized view component 245 above, a clinician may desire to display her personalized view to allow other clinicians insight into a particular condition of or treatment for the patient. As mentioned above, the clinician may have a different default view of the dashboard and perspectives and gadgets associated with that view that are normally unavailable to other clinicians. For example, intensive care unit (ICU) perspectives may include an ICU SUMMARY, MEDICATIONS, HEMODYNAMICS, I/O 7 DAY, or INFUSION DOCUMENTATION perspectives that do not appear in other clinicians' displays. Gadgets associated with those perspectives may allow a clinician to see trends, graphs, real-time measurements, scroll bars to navigate certain views, and the like. Perspectives component 260 enables these perspectives and gadgets on the dashboard for display to other clinicians and family members.

In one embodiment, role view component 265 displays a role view associated with a role of another clinician. For example, the attending physician may desire to see a view that is typically only displayed on an ICU clinician's device. Role view component 265 allows the attending physician to select and display on the dashboard the view associated with the ICU role.

Figure 3D:
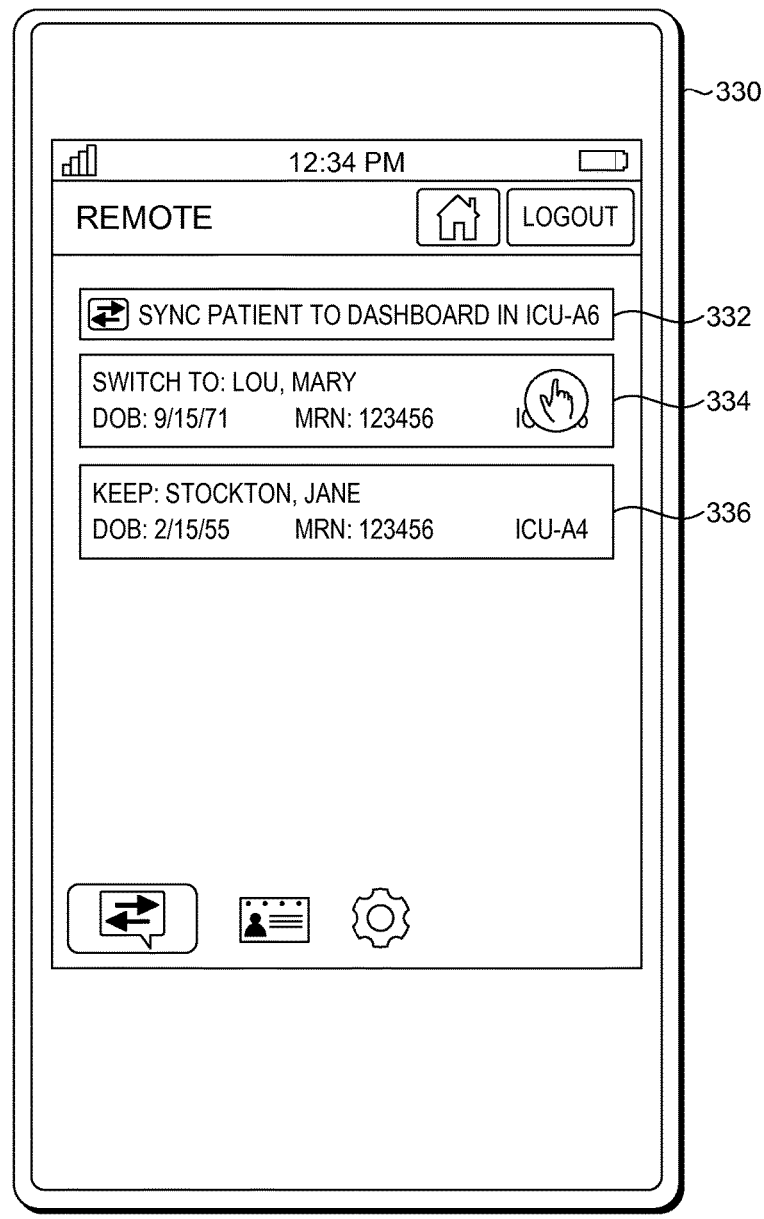

Referring now to FIGS. 3A-3C, in illustrative screen displays 300, 310, 320, and 330, displays associated with various devices are depicted. Dashboard display 300 displays the view of the dashboard in a location associated with a patient. Dashboard display 300 may, in one embodiment, be manually configured to display the dashboard associated with the patient. In another embodiment, dashboard display 300 may display the dashboard associated with the patient based on presence awareness, discussed above. Device displays 310, 320, and 330 represent displays associated with various devices utilized by clinicians. These devices may, in various embodiments, include a workstation on wheels (WOW), a mobile computing device, a handheld computer device, and the like.

A first display area 312, 322, and 332 on each of device displays 310, 320, and 330 displays a notification that a wrong chart is open for a location. A clinician possessing one of the devices associated with device displays 310, 320, or 330 may have entered the location from a previous location and still have the chart associated with the previous location open on her device. Thus, by utilizing presence awareness discussed above, the first display area 312, 322, and 332 displays a notification asking the clinician to synchronize the patient associated with the chart on the device to the dashboard for a given patient or in a given location.

A second display area 314, 324, and 334 on each of device displays 310, 320, and 330 displays a prompt allowing a clinician to synchronize the chart on the device with the dashboard for a given patient. A third display area 316, 326, and 336 on each of device displays 310, 320, and 330 displays a prompt allowing a clinician to keep the chart on the device with the dashboard for a previous patient. This may be useful if a clinician needs additional time to continue charting for or to refer to the previous patient's chart.

Figure 4:
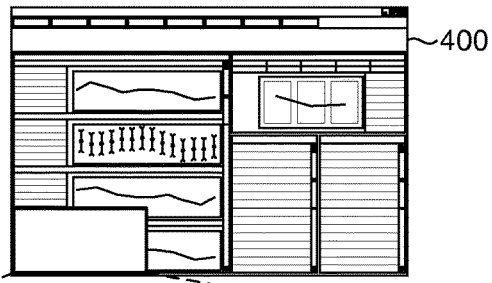
FIG. 4 is an illustrative graphical user interface display of the dashboard remote, in accordance with an embodiment of the present invention.
Figure 4:
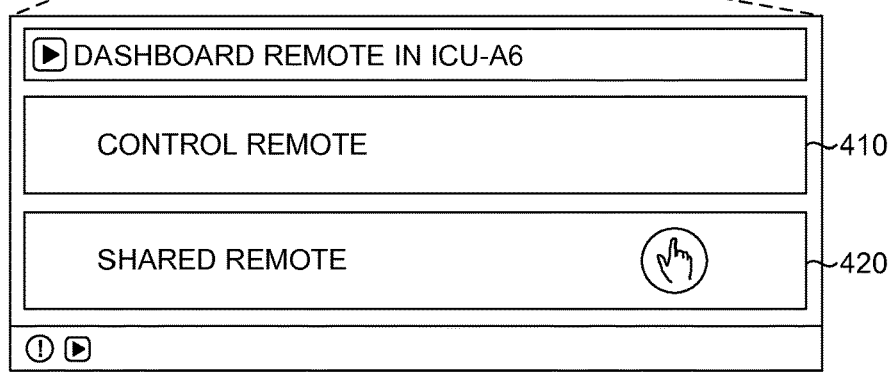
Figure 5:
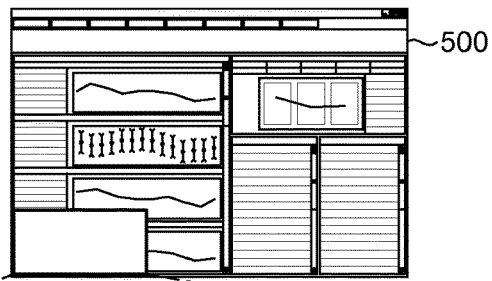
FIG. 5 is an illustrative graphical user interface display of sharing control of the dashboard with another clinician, in accordance with an embodiment of the present invention.
Figure 5:
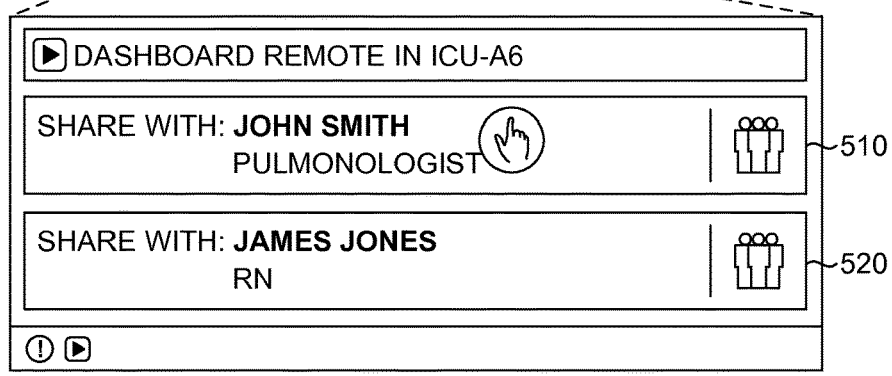

Referring now to FIGS. 4 and 5, illustrative screen displays depict the dashboard remote 400 and sharing the dashboard 500 with other clinicians, respectively, in accordance with embodiments of the present invention. Third display area 400, 500 displays a clinician view of the dashboard. Options in third display area 400 include an option to control the remote 410 or an option to share the remote 420 with other clinicians. If a clinician selects the option to share the remote 420, the available clinicians appear in a list allowing the clinician to select the desired clinicians. Selectable icons or buttons 510, 520 appear next to the available clinicians names, and upon selection, control of the dashboard is shared with the selected clinicians.

Figure 6A:
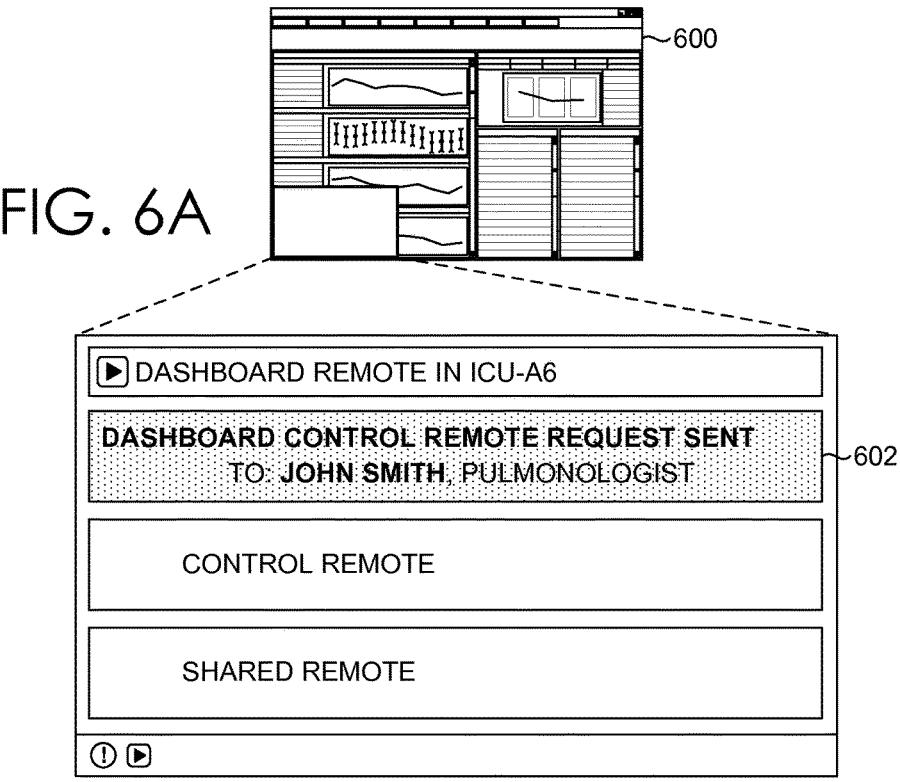
FIGS. 6A-6C are illustrative graphical user interface displays of requesting dashboard control, in accordance with an embodiment of the present invention.
Figure 6B:
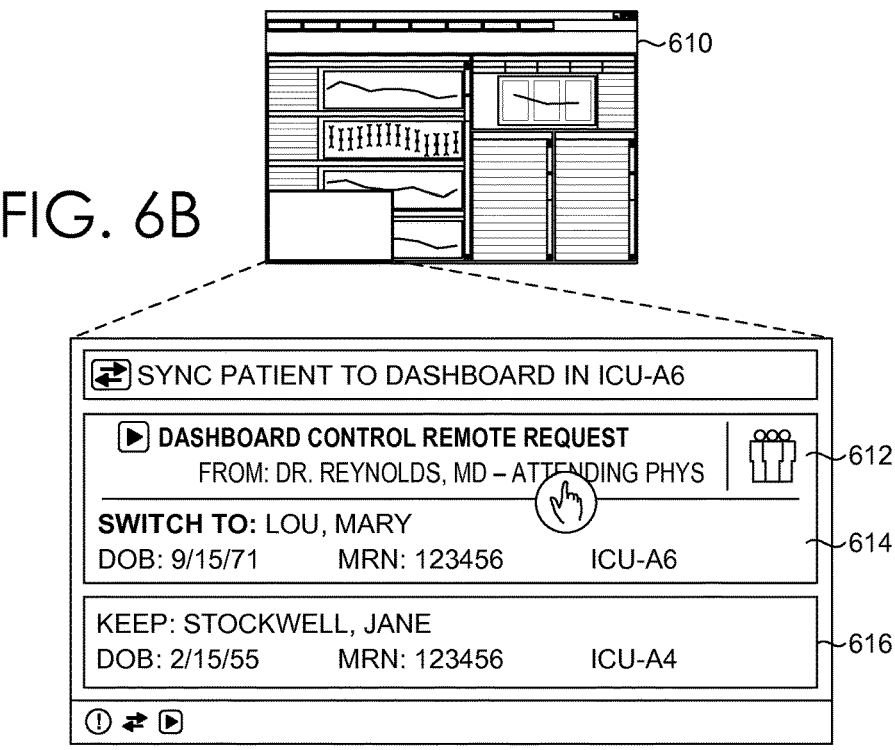
Figure 6C:
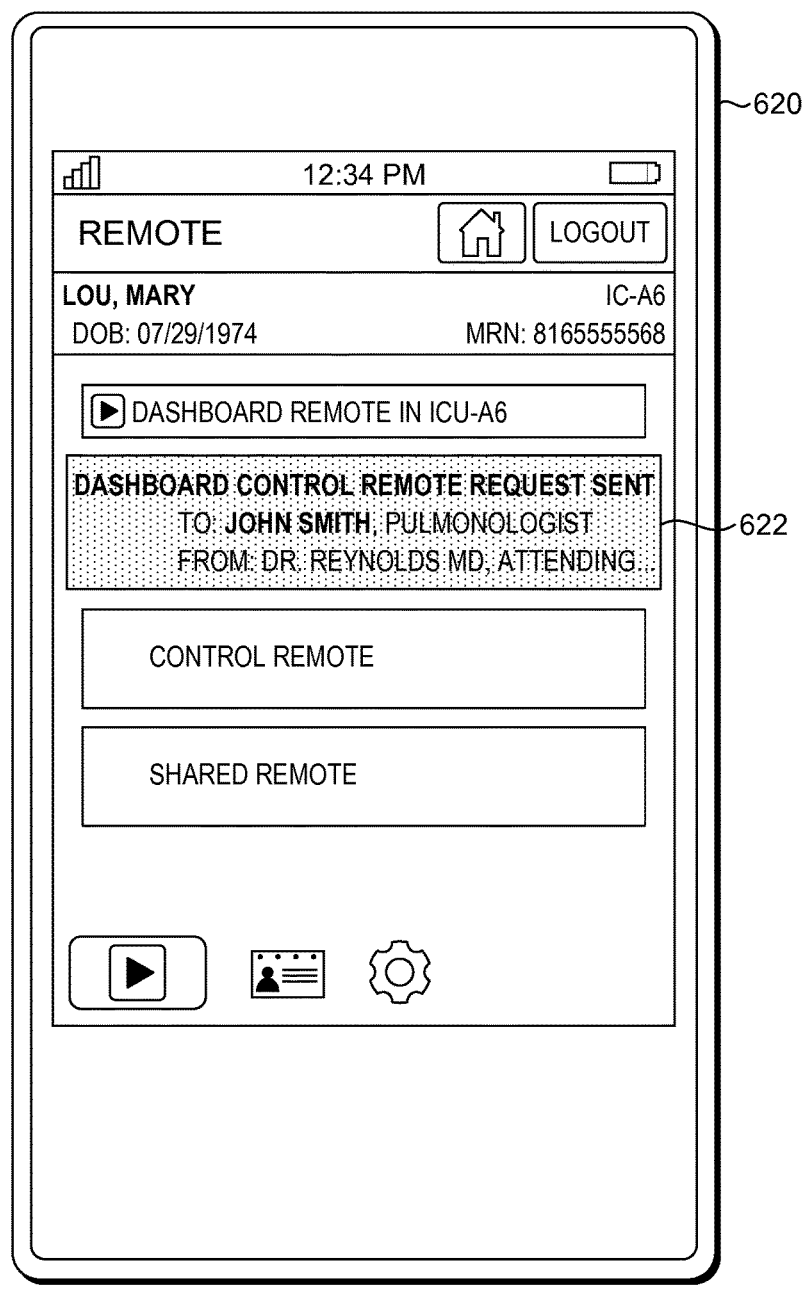

Referring now to FIGS. 6A-6C, illustrative screen displays depict displays 600, 610, 620 of requesting dashboard control, in accordance with embodiments of the present invention. When a clinician requests that another clinician take control of the dashboard, an indication 602 on the device of the requesting clinician notifies the clinician that her request to share the remote has been sent to the clinician that is being requested to control the dashboard. On other devices that currently display a view of the dashboard, a notification 612, 622 notifies the other clinicians that such a request has been made. A fourth display area displays the request to share control of the dashboard with a second clinician utilizing a second device. On the device associated with the clinician that is being requested to control the dashboard, options are available for that clinician. The clinician can select to switch to the chart associated with the request by selecting a switch to button 614 or the clinician can select to maintain the display of the current chart on the clinician's device, thereby denying the request to control the dashboard, by selecting the keep button 616.

Figure 7:
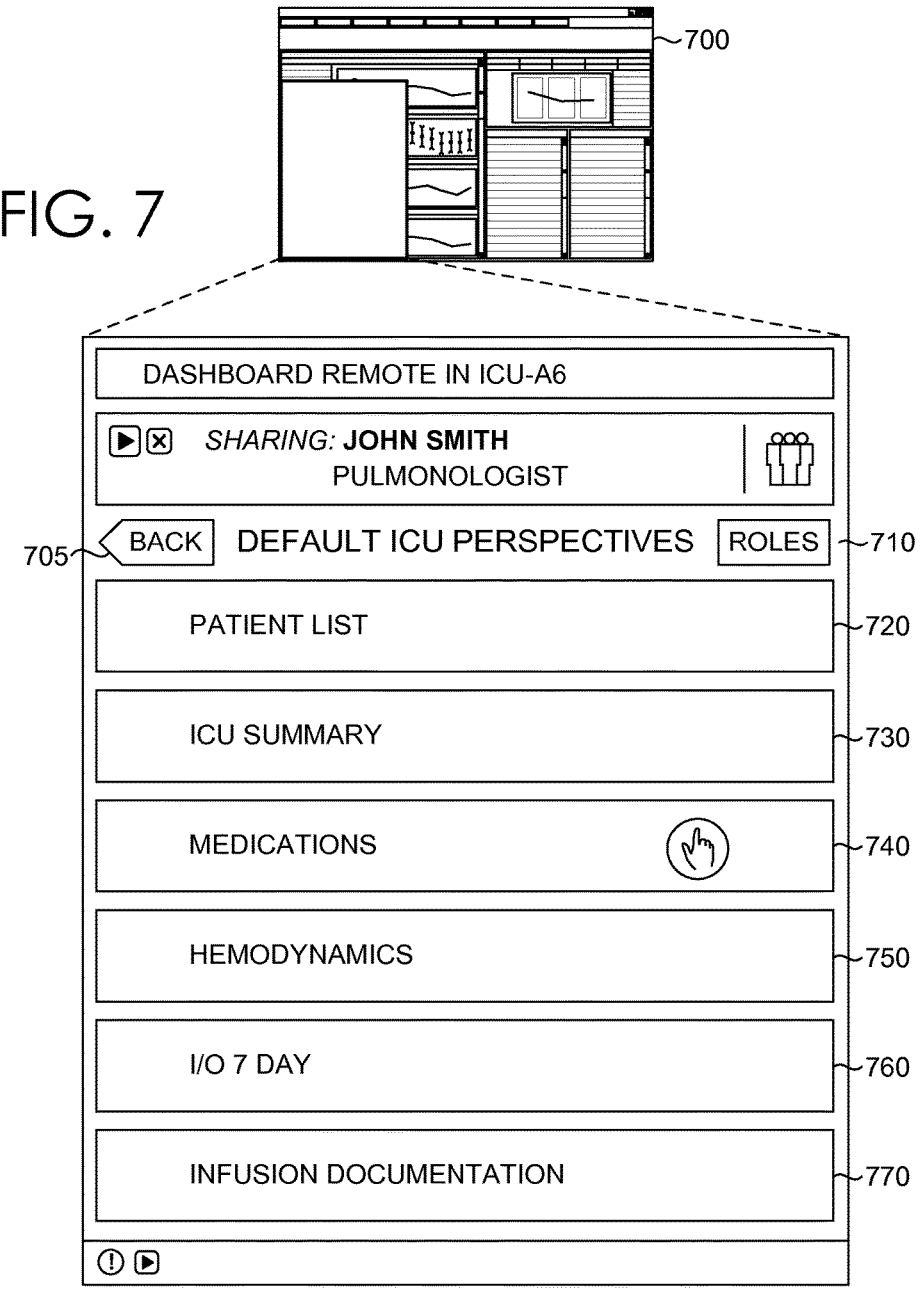
FIG. 7 is an illustrative graphical user interface display of perspectives associated with a role, in accordance with an embodiment of the present invention.

Referring now to FIG. 7, an illustrative screen display depicts perspectives associate with a role, in accordance with an embodiment of the present invention. As mentioned above, the clinician may have a different default view of the dashboard and perspectives and gadgets associated with that view that are normally unavailable to other clinicians. When a clinician desires to display her personalized view of a chart on the dashboard to allow other clinicians insight into a particular condition of or treatment for the patient, a fifth display area 710 displays a personalized view associated with her role. This personalized view may be default perspectives that include, for example, in an ICU setting, PATIENT LIST 720, ICU SUMMARY 730, MEDICATIONS 740, HEMODYNAMICS 750, I/O 7 DAY 760, AND INFUSION DOCUMENTATION 770. A clinician may also determine that it is no longer necessary to show perspectives associated with her role and select a BACK button 705. Gadgets associated with those perspectives may allow a clinician to see trends, graphs, real-time measurements, scroll bars to navigate certain views, and the like.

Figure 8:
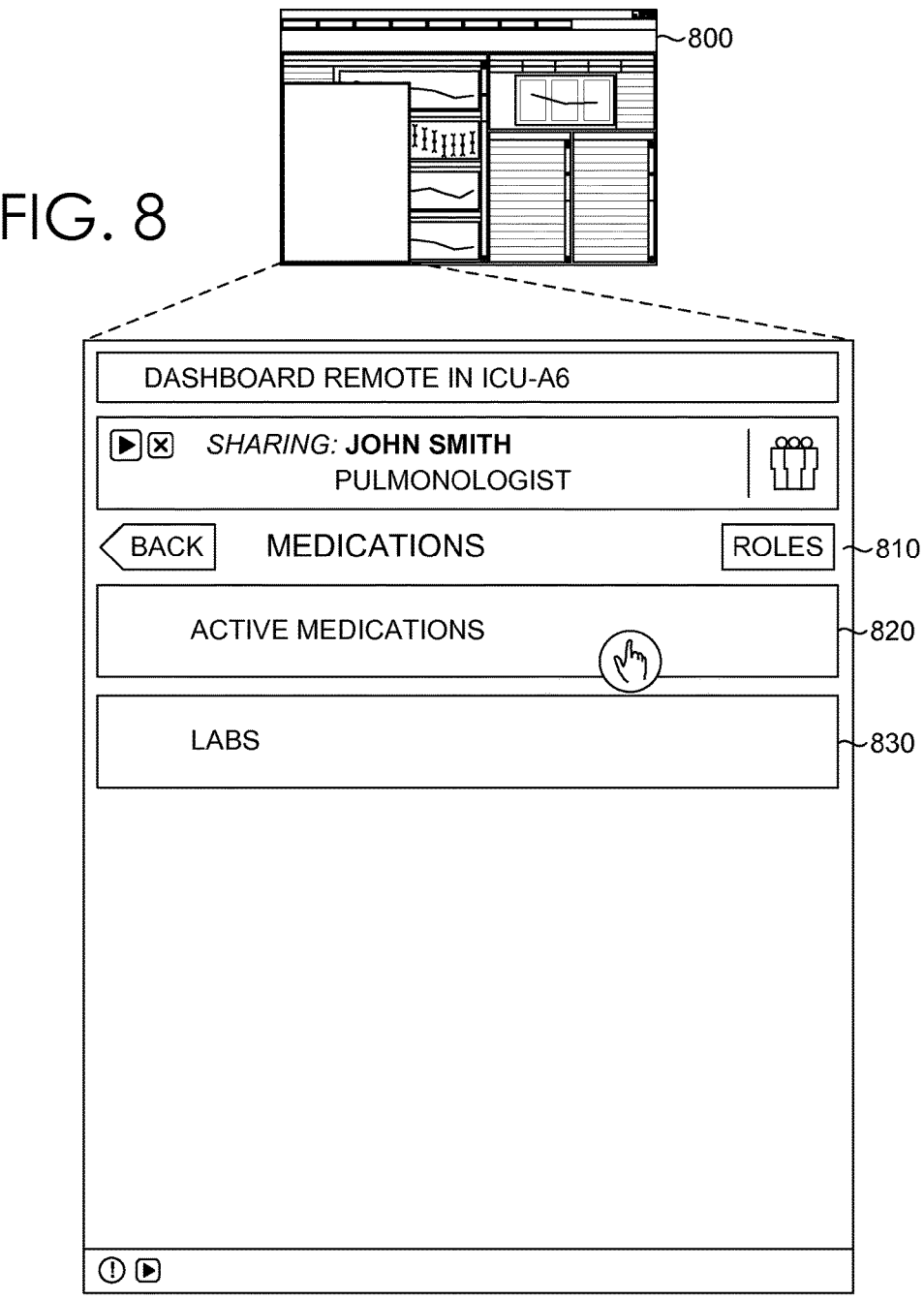
FIGS. 8 and 9 are illustrative graphical user interface displays of personalized views, in accordance with an embodiment of the present invention.
Figure 9:
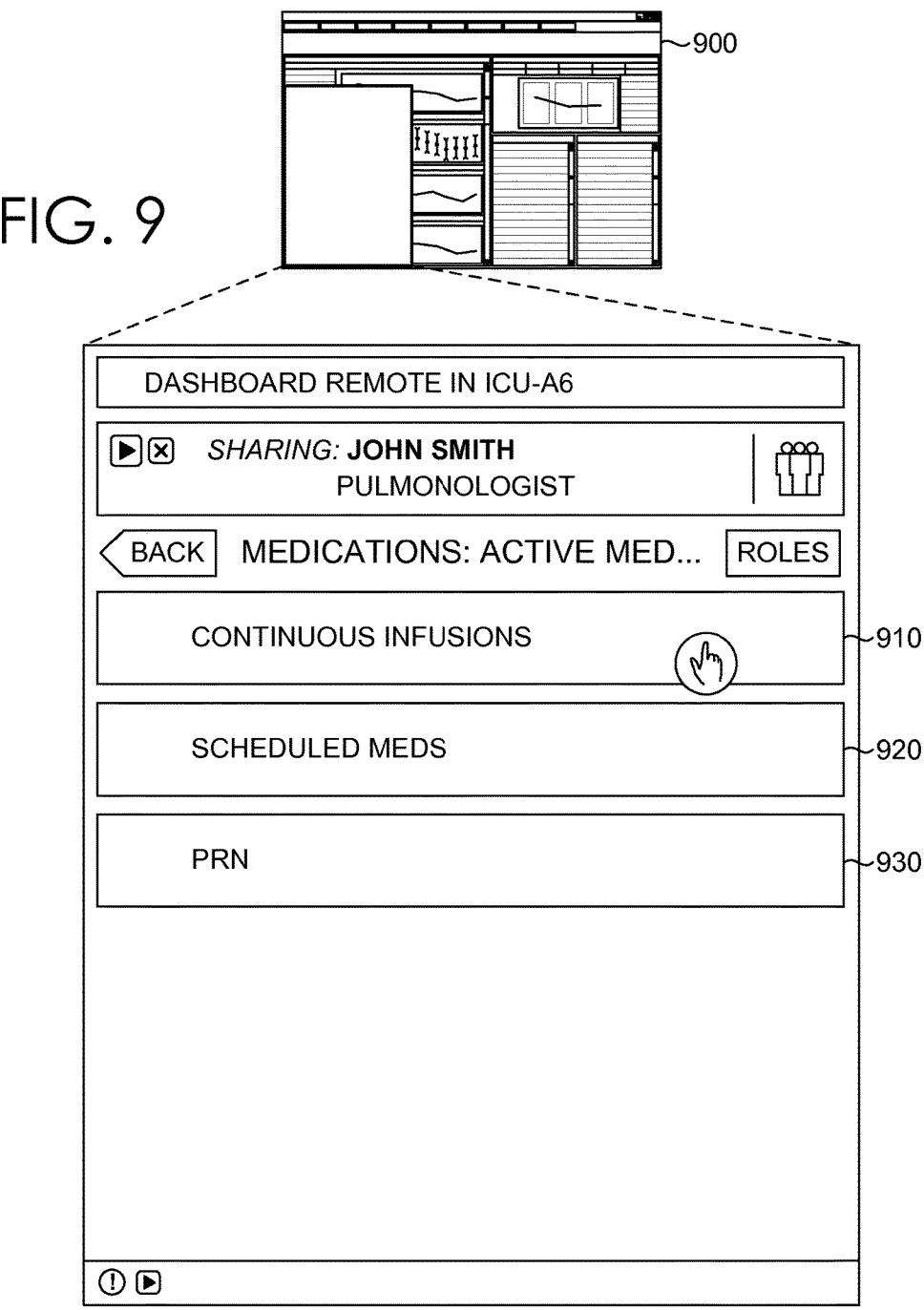

Referring now to FIGS. 8 and 9, illustrative screen displays depict personalized views 800, 900, in accordance with embodiments of the present invention. For example, the clinician may have selected MEDICATIONS 740 from the display in FIG. 7. The MEDICATIONS personalized view 810 is now displayed on the dashboard. Options to select ACTIVE MEDICATIONS 820 or LABS 830 are now available. Upon selecting ACTIVE MEDICATIONS 820, options to select CONTINUOUS INFUSIONS 910, SCHEDULED MEDS 920, or PRN 930 are now available.

Figure 10:
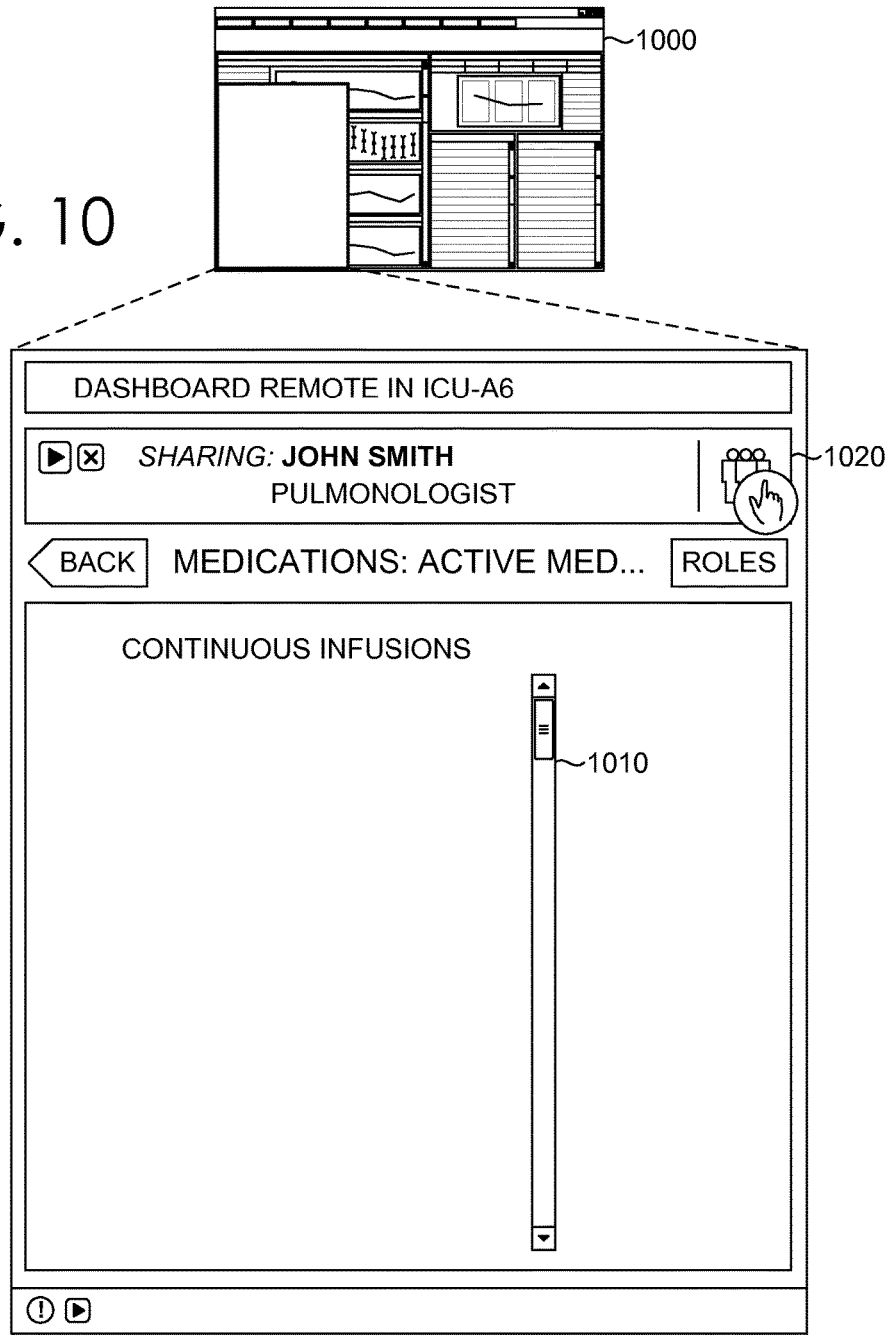
FIGS. 10 and 11A-11B are illustrative graphical user interface displays of sharing personalized views, in accordance with an embodiment of the present invention.
Figure 11B:
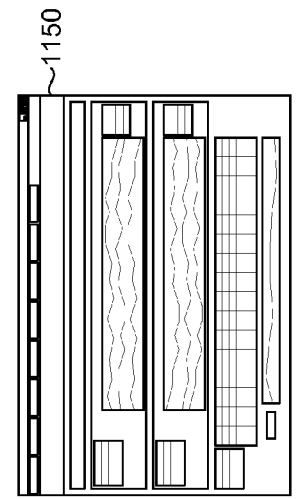
Figure 11A:
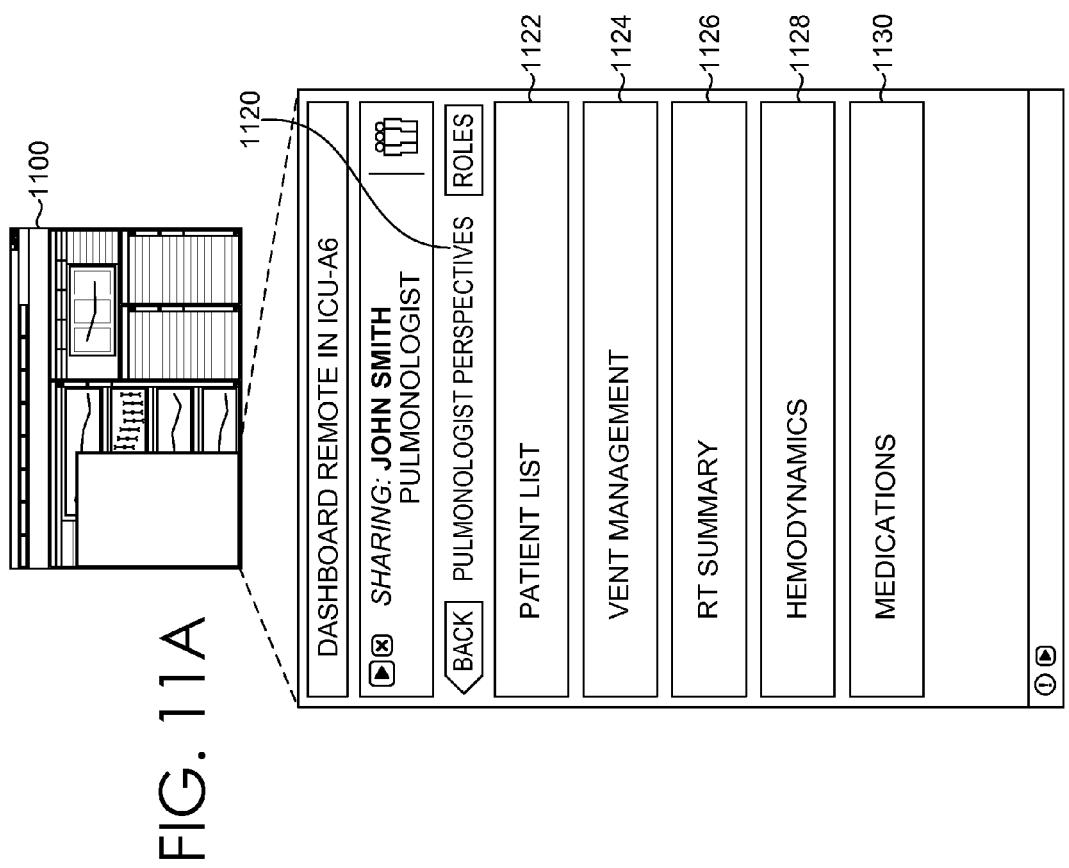

Referring now to FIGS. 10 and 11A-11B, illustrative screen display depicts personalized views 1000, 1100, 1150 in accordance with embodiments of the present invention. As noted above, each of these perspectives may include various gadgets to aid in viewing a particular display or perspective. For example, a scroll bar 1010 allows the sharing clinician and other clinicians to navigate items displayed on the dashboard via the personalized view such as through a list of continuous infusions. A share button 1020 allows a clinician to share these personalized views with other clinicians. Other perspectives, such as PULMONOLOGIST PERSPECTIVES 1120, in one embodiment, allow a clinician to view displays of a PATIENT LIST 1122, VENT MANAGEMENT 1124, RT SUMMARY 1126, HEMODYNAMICS 1128, or MEDICATIONS 1130. Upon selection of one of these perspectives, the dashboard may display various charts or graphs 1150 associated with the selected perspective.

Figure 12A:
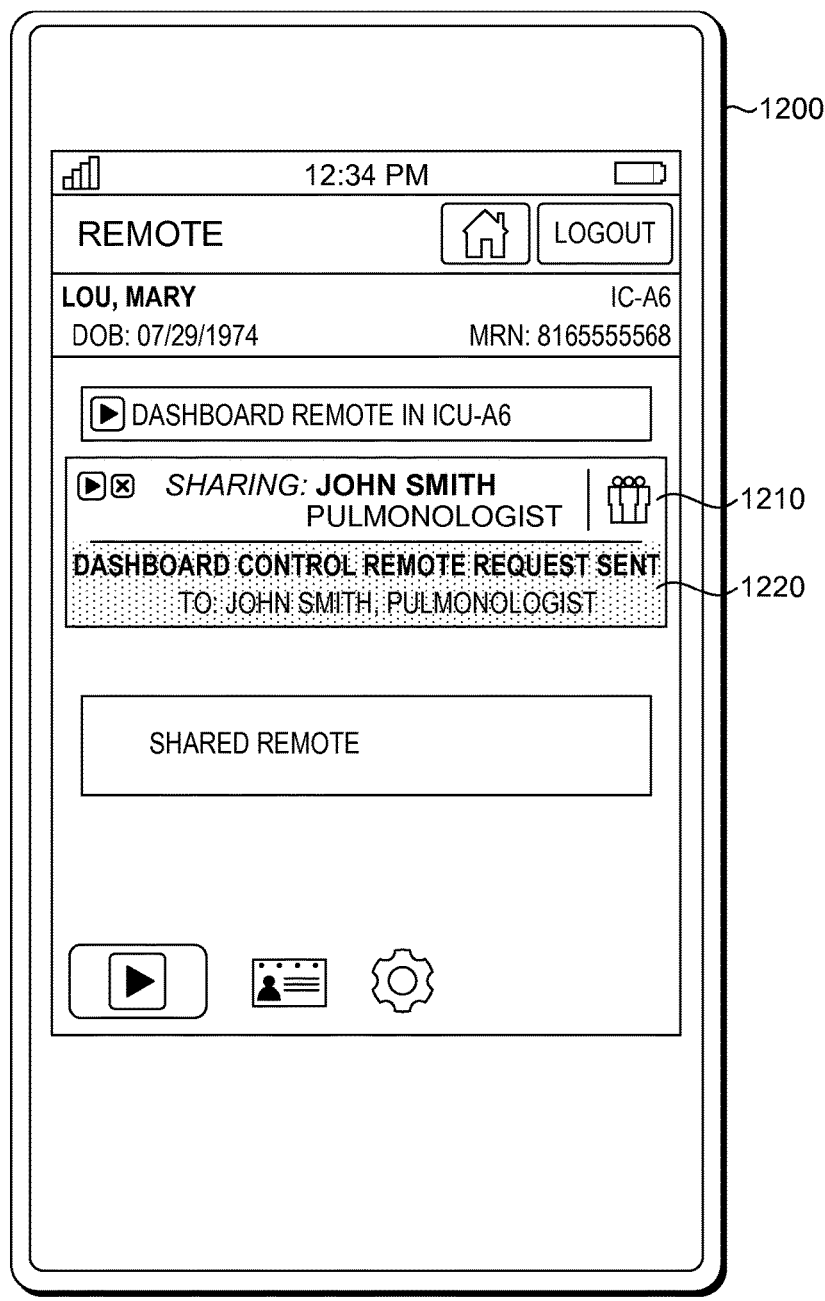
Figure 13:
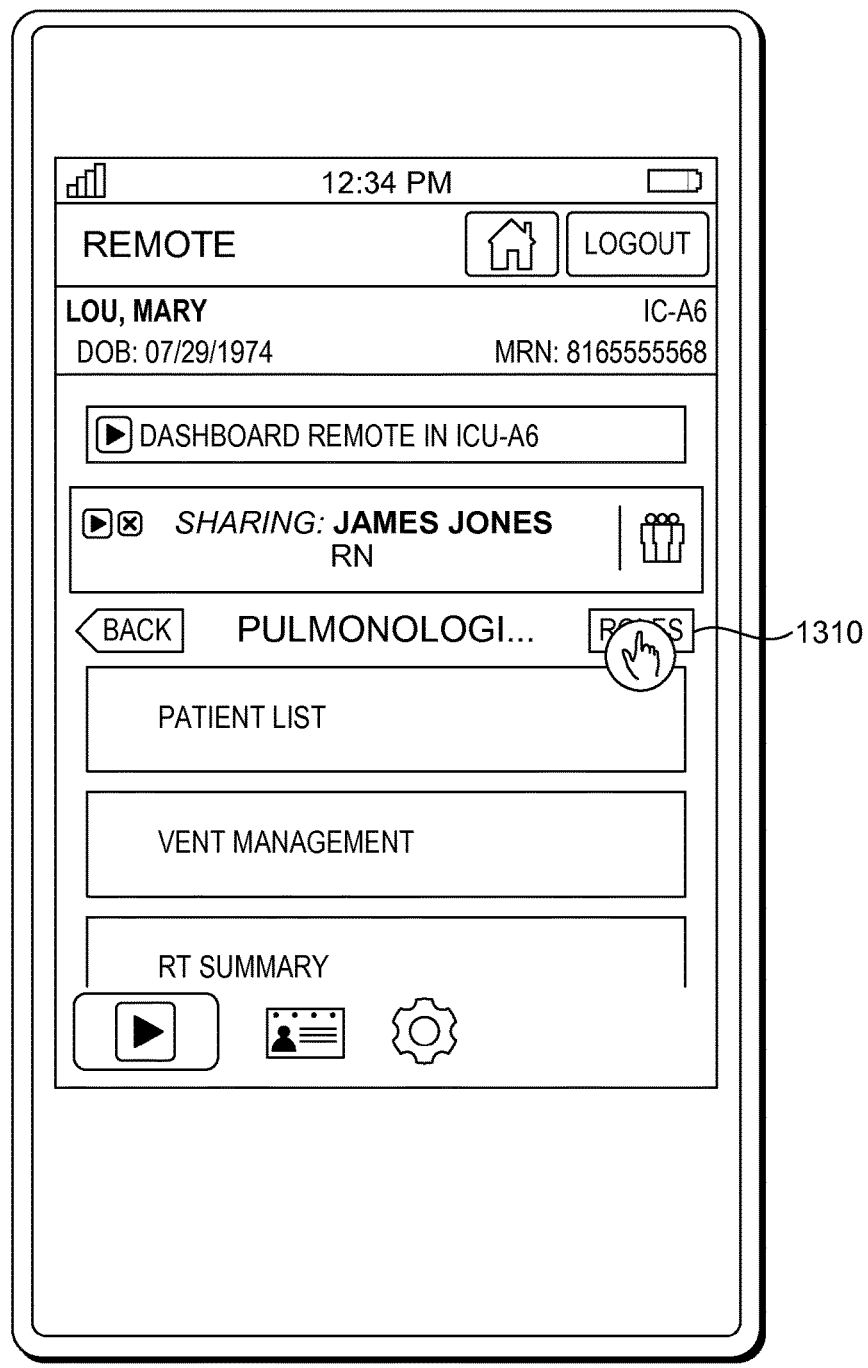
FIGS. 13 and 14A-14C are illustrative graphical user interface displays of changing perspectives, in accordance with an embodiment of the present invention.
Figure 14A:
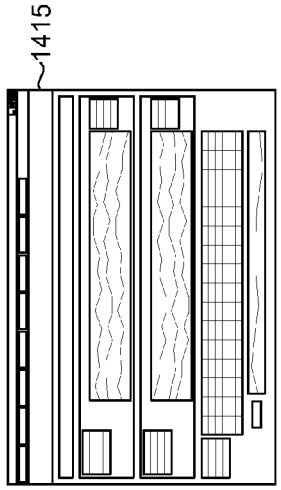
Figure 14B:
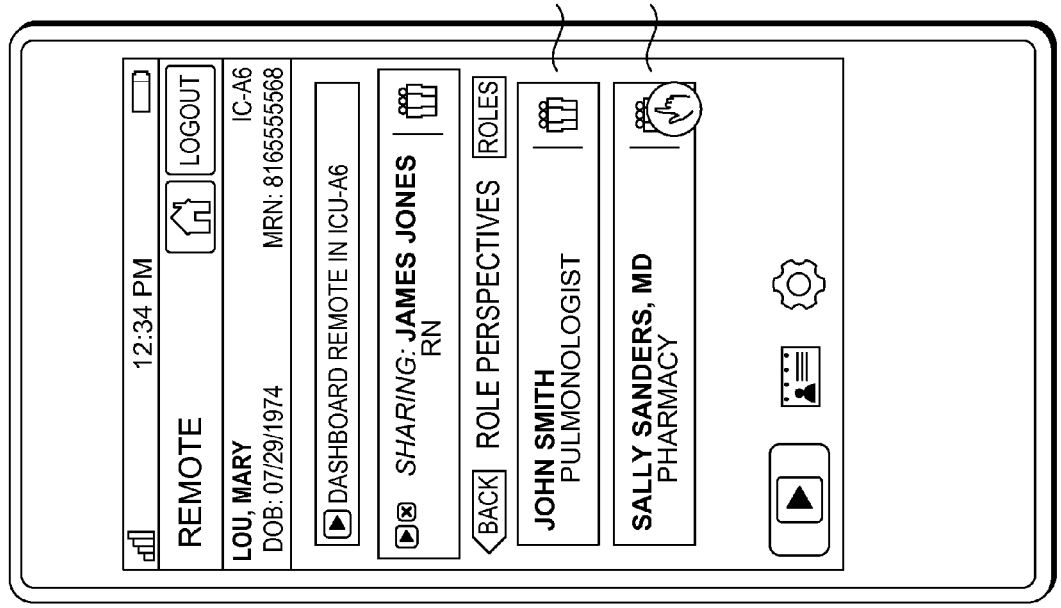
Figure 14C:
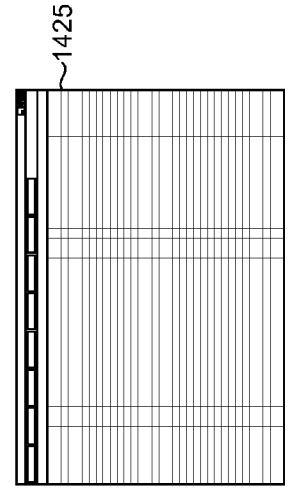

Referring now to FIGS. 12A-12C, illustrative screen displays depict sharing dashboard control, in accordance with embodiments of the present invention. A clinician utilizing a device 1200 may desire to share control 1210 of the dashboard with another clinician. A request display 1220 indicates that a request has been sent to the other clinician. The clinician that is being requested to control the dashboard receives the share request 1230 along with a notification 1240 identifying the requesting clinician. If the clinician accepts the share request, a perspective associated with the accepting clinician's role may be displayed on the dashboard 1250.

Referring now to FIGS. 13 and 14A-C, illustrative screen displays depict changing perspectives, in accordance with embodiments of the present invention. For example, the clinician currently in control of the dashboard may desire to see a view that is typically only displayed on a device associated with clinician with a different role. ROLES button 1310 allows the controlling clinician to select and display on the dashboard the view associated with another role. The clinician can select the PULMONOLOGIST role 1410 and the dashboard 1415 displays the view associated with the role of a pulmonologist. Or the clinician can select the PHARMACY role 1420 and the dashboard 1425 displays the view associated with the role of a pharmacy clinician. As can be appreciated, any number of dashboard views may be available for any number of roles.

Figure 15A:
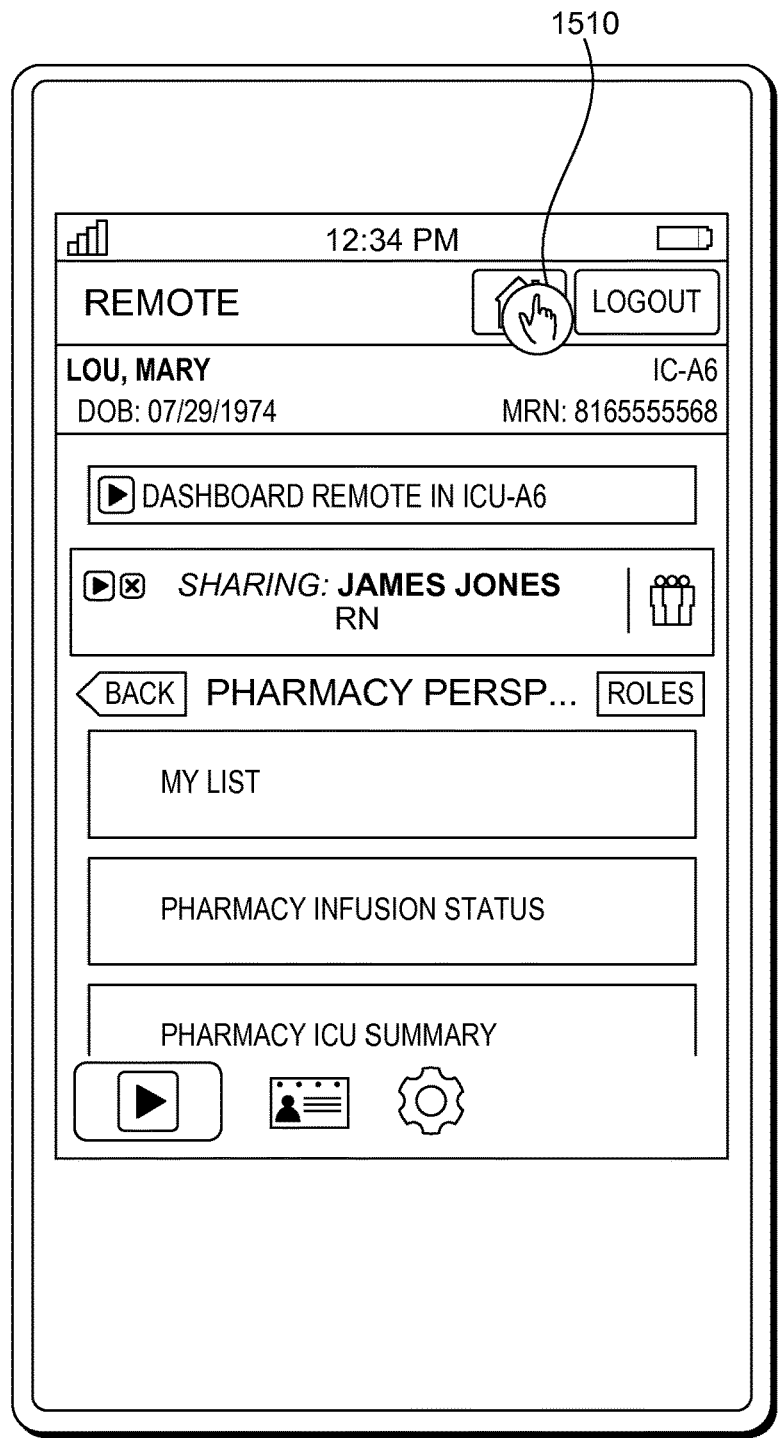
FIGS. 15A-15C are illustrative graphical user interface displays of returning control of the dashboard to the attending clinician, in accordance with an embodiment of the present invention.
Figure 15B:
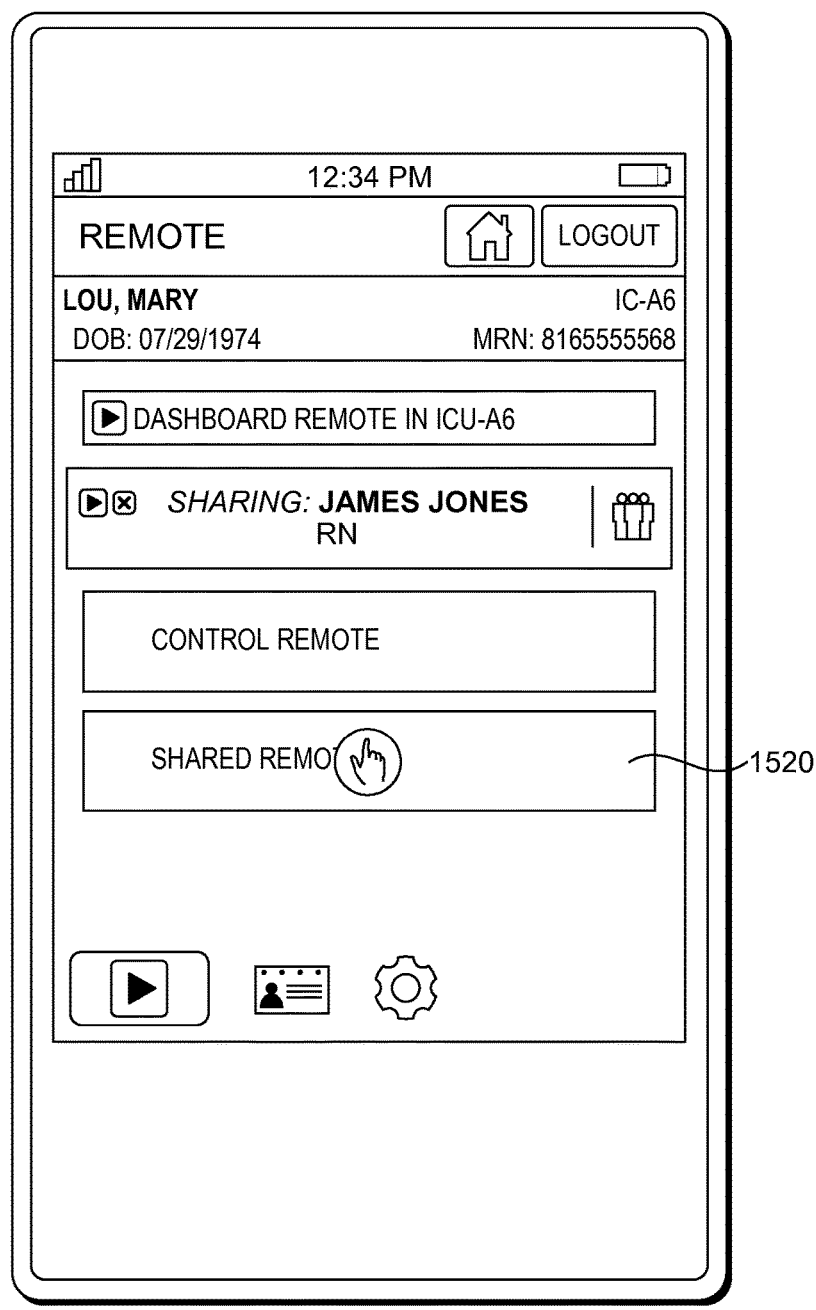
Figure 15C:
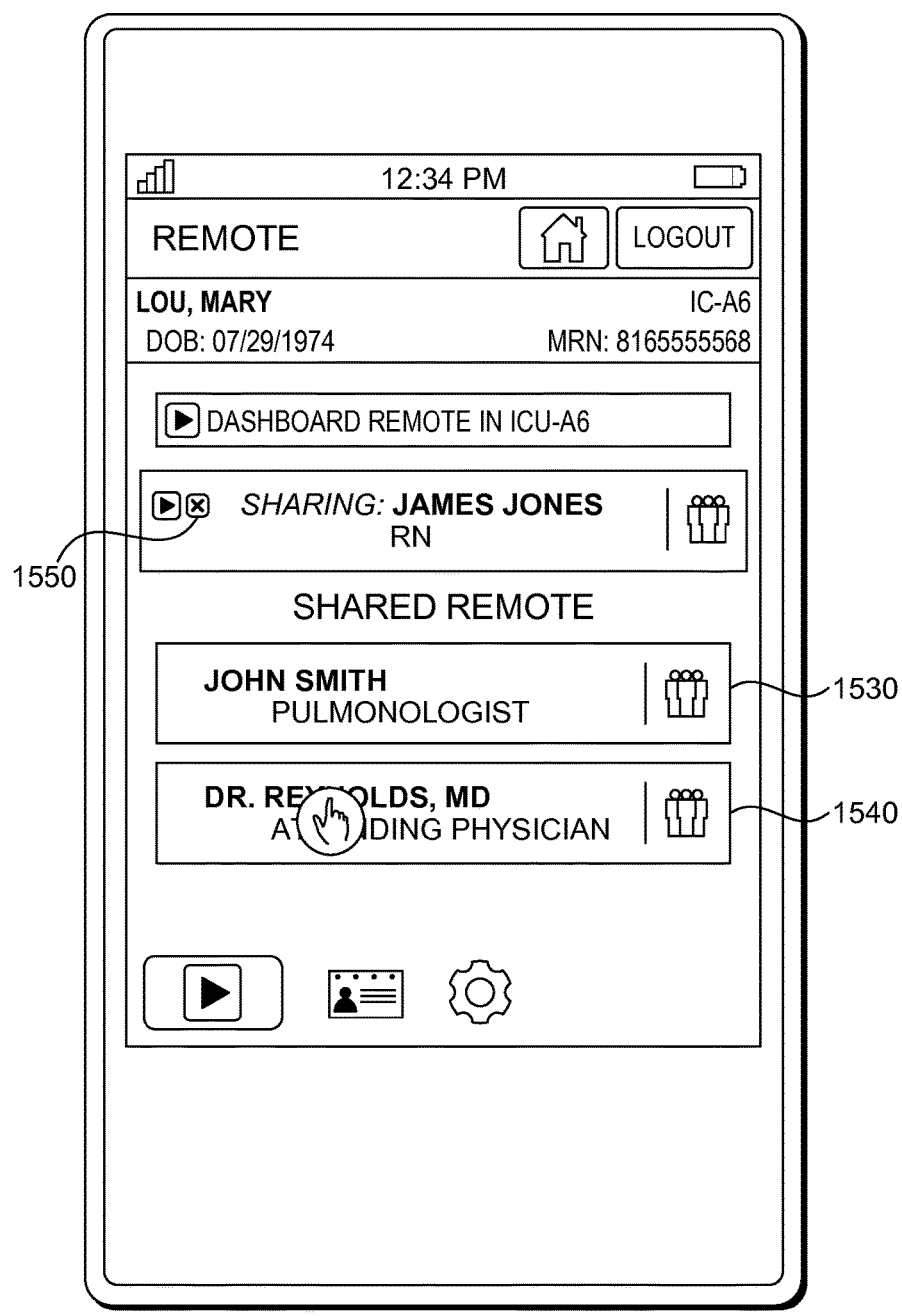

Referring now to FIGS. 15A-15C, illustrative screen displays depict returning control of the dashboard, in accordance with embodiments of the present invention. A clinician currently controlling the dashboard remote can select the home button 1510 to return to the main menu on the remote. The clinician can select the shared remote button 1520 to select another clinician 1530, 1540 to return control of the dashboard remote. In this example, the clinician selects to return control of the dashboard remote to the attending physician. In one embodiment, the clinician selects the end sharing session button 1550 to end the dashboard session on the clinician's device. In one embodiment, ending the dashboard session automatically returns control to the attending physician. In another embodiment, ending the dashboard session automatically returns control of the dashboard remote to the clinician that previously controlled the dashboard remote. In another embodiment, ending the dashboard session returns control of the dashboard remote to the dashboard itself and control of the dashboard is available to any clinician selecting to control the dashboard remote.

Figure 16:
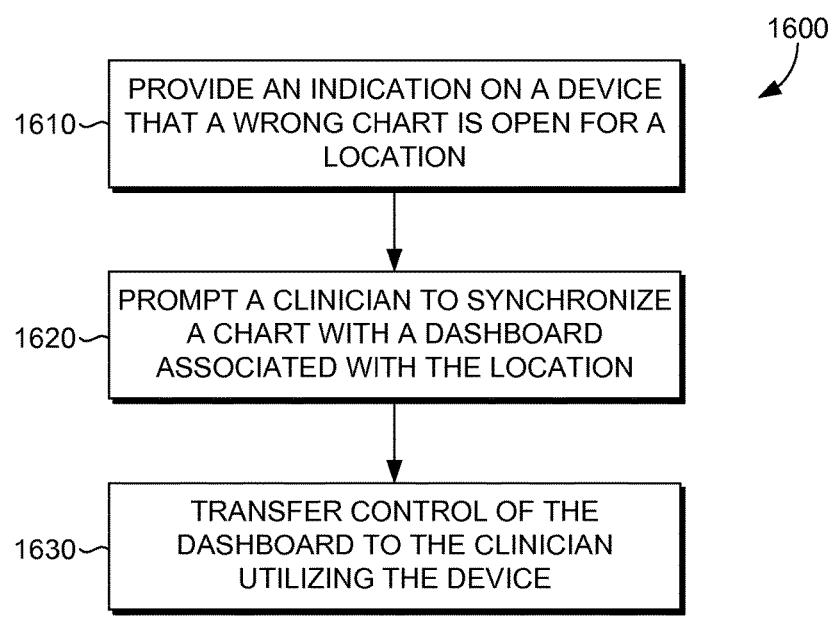
FIG. 16 is a flow diagram showing a method for facilitating multidevice collaboration, in accordance with an embodiment of the present invention.

Referring now to FIG. 16, an illustrative flow diagram 1600 is shown of a method for facilitating multidevice collaboration. At step 1610, an indication on a first device that a wrong chart is open for a location. A first clinician is prompted to synchronize a chart with a dashboard associated with the location at step 1620. In one embodiment, the presence of the device or clinician near the location is compared to the chart that should be open on the clinician's device for that location. In another embodiment, the presence of the device or clinician is utilized in conjunction with the presence of the nearest patient or dashboard to determine which chart should be open on the clinician's device. At step 1630, control of the dashboard is transferred to the first clinician utilizing the first device. In one embodiment, transferring control of the dashboard allows the first clinician to modify the views on the dashboard utilizing the first device.

In one embodiment, a personalized view associated with a role of the first clinician is displayed. In one embodiment, a role view associated with a role of another clinician is displayed. In another embodiment, perspectives and gadgets associated with the role are enabled. In one embodiment, the display of the perspectives and gadgets are restricted according to an audience. For example, the clinician may be collaborating with other clinicians and desire to display very specific or sensitive items. However, if on the other hand, the clinician is educating the patient or family regarding the condition or treatment of the patient, the clinician may desire to display only high level or different information.

In one embodiment, a request is received from a second clinician to share control of the dashboard utilizing a second device. For example, another clinician may enter the location or presence of the patient associated with the dashboard. To effectively collaborate with the first clinician, the second clinician may need to draw the attention of the first clinician to a particular item on the dashboard. The second clinician submits a request to control the dashboard. In another example, the first clinician may desire to transfer control of the dashboard to the second clinician for similar reasons. In this embodiment, a request is received from the first clinician to transfer control of the dashboard to the second clinician. In another embodiment, the request is communicated to the second device operated by the second clinician so the second clinician may take the appropriate action. In one embodiment, the second clinician acknowledges the request. In one embodiment, such acknowledgement transfers control of the dashboard to the second device. In one embodiment, transferring control of the dashboard allows the second clinician to modify the view on the dashboard utilizing the second device.

In another embodiment, the request is communicated to a third device operated by a third clinician. For example, three or more clinicians may be collaborating. Notification of such requests allows each clinician to recognize which clinician is currently controlling the dashboard.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

Having thus described the invention, what is claimed is:
1. One or more computer hardware storage media (the "media") storing computer-executable instructions that, when executed by one or more computing devices, cause the one or more computing devices to perform a method that facilitates multidevice collaboration, the method comprising:
    providing a notification on a first device of a first clinician configured for viewing and/or charting patient information during patient care that a wrong chart is open for a location;
    prompting the first clinician, with the first device, to synchronize a chart with a dashboard at the location, wherein the chart is associated with a patient at the location; and
    transferring control of the dashboard to the first clinician utilizing the first device so that the first clinician controls the dashboard using the first device.

2. The media of claim 1, further comprising receiving a request from a second clinician to share control of the dashboard utilizing a second device.

3. The media of claim 2, further comprising communicating the request to the first device operated by the first clinician.

4. The media of claim 1, further comprising receiving a request from the first clinician to transfer control of the dashboard to a second clinician.

5. The media of claim 4, further comprising communicating the request to a second device operated by the second clinician.

6. The media of claim 5, further comprising receiving acknowledgment of the request.

7. The media of claim 5, further comprising transferring control of the dashboard to the second device.

8. The media of claim 7, wherein transferring control of the dashboard allows the second clinician to modify the views on the dashboard utilizing the second device.

9. The media of claim 1, wherein transferring control of the dashboard allows the first clinician to modify the views on the dashboard utilizing the first device.

10. The media of claim 1, further comprising displaying a personalized view associated with a role the first clinician.

11. The media of claim 10, further comprising enabling perspectives and gadgets associated with the role.

12. The media of claim 11, further comprising restricting the display of the perspectives and gadgets according to an audience.

13. The media of claim 1, further comprising displaying a role view associated with a role of another clinician.

14. A computer system for facilitating multidevice collaboration comprising;
    a processor coupled to a computer storage medium, the computer storage medium having stored thereon a plurality of computer software components executable by the processor, the computer software components comprising:
    a notification prompt component that notifies a first device of a first clinician configured for viewing and/or charting patient information during patient care that a wrong chart is open for a location;
    a synchronization component that prompts the first clinician to synchronize a chart with a dashboard at the location, wherein the chart is associated with a patient at the location;
    a transfer component that transfers control of the dashboard to the first clinician utilizing the first device so that the first clinician controls the dashboard using the first device;
    a modification component that allows the first clinician to modify views on the dashboard utilizing the first device; and
    a personalized view component that displays a personalized view associated with a role of the first clinician.

15. The computer system of claim 14, further comprising a request component that receives requests from a second clinician requesting control of the dashboard utilizing a second device.

16. The computer system of claim 15, further comprising a share component that transfers control of the dashboard to the second clinician utilizing the second device.

17. The computer system of claim 14, further comprising a perspectives component that enables perspectives and gadgets associated with the role.

18. The computer system of claim 14, further comprising a role view component that displays a role view associated with a role of another clinician.

19. Computer hardware storage media having computer-executable instructions embodied thereon that, when executed by one or more computing devices, cause the one or more computing devices to produce a graphical user interface (GUI) to facilitate multidevice collaboration, the GUI comprising:
    a first display area that displays a first notification that a wrong chart is open on a device configured for viewing and/or charting patient information during patient care for a location, and asks a first clinician to synchronize a patient associated with a chart on the device to a dashboard in a given location;
    a second display area that displays a second notification for the first clinician to synchronize the chart with the dashboard associated with the location;
    a third display area that displays a clinician view of the dashboard wherein the first clinician controls the dashboard with the device;
    a fourth display area that displays a request from a second clinician to share control of the dashboard utilizing a second device; and
    a fifth display area that displays a personalized view associated with a role of the first clinician.

20. The first device of claim 1, further comprising a mobile device.

* * * * *

UNITED STATES PATENT AND TRADEMARK OFFICE
CERTIFICATE OF CORRECTION

PATENT NO. : 10,402,926 B2
APPLICATION NO. : 13/341480
DATED : September 3, 2019
INVENTOR(S) : Lisa Kelly et al.

Page 1 of 1

It is certified that error appears in the above-identified patent and that said Letters Patent is hereby corrected as shown below:

On the Title Page

Item (56), Column 02, Other Publications, Line 02: Please remove "Gogple" and replace with --Google--.

In the Claims

Column 13, Line 38: Please remove "a role the" and replace with --a role of the--.

Signed and Sealed this
Twenty-second Day of October, 2019

Andrei Iancu
*Director of the United States Patent and Trademark Office*